United States Patent [19]

Tantram et al.

[11] Patent Number: 4,633,704

[45] Date of Patent: Jan. 6, 1987

[54] GAS SENSOR

[75] Inventors: Anthony D. S. Tantram, Great Bookham; Yat S. Chan, London, both of England

[73] Assignee: City Technology Limited, England

[21] Appl. No.: 857,501

[22] Filed: Apr. 21, 1986

Related U.S. Application Data

[63] Continuation of Ser. No. 723,722, Apr. 17, 1985, abandoned, which is a continuation of Ser. No. 495,328, May 17, 1983, abandoned.

[30] Foreign Application Priority Data

May 26, 1982 [GB] United Kingdom ............... 8215426

[51] Int. Cl.⁴ ........................................... G01N 27/28
[52] U.S. Cl. ...................................... 73/23; 204/1 T; 204/415
[58] Field of Search ................... 73/23; 204/1 T, 415; 422/58, 88, 98

[56] References Cited

U.S. PATENT DOCUMENTS

| 2,913,386 | 11/1959 | Clark | 204/415 |
| 3,950,980 | 4/1976 | Braun et al. | 73/23 |
| 4,267,023 | 5/1981 | Frant et al. | 73/23 |
| 4,324,632 | 4/1982 | Tantram et al. | 204/415 |
| 4,406,770 | 9/1983 | Chan et al. | 204/415 |

Primary Examiner—Stephen A. Kreitman
Assistant Examiner—John E. Chapman, Jr.
Attorney, Agent, or Firm—Sughrue, Mion, Zinn, Macpeak, and Seas

[57] ABSTRACT

The housing 1 of a gas sensor carries a diffusion barrier 2 for restricting the access of gas to the sensing element 4 and a filter 3 mounted between the diffusion barrier 2 and the sensing element 4. As a result, gas reaching the filter 3 must first pass through the diffusion barrier 2 so that its flux is substantially reduced and the life of the filter is increased correspondingly.

3 Claims, 3 Drawing Figures

GAS SENSOR

This is a continuation of application Ser. No. 723,722, filed Apr. 17, 1985, abandoned, which is a continuation of application Ser. No. 495,328, filed May 17, 1983, abandoned.

This invention relates to the detection and measurement of gases.

There is an increasing demand for gas sensing instruments for safety monitoring, pollution control, fire detection, flue gas analysis and so forth. There is a special demand for portable, relatively inexpensive instruments and, for these to fit the application requirements, small compact, light weight, robust, reliable and relatively inexpensive sensors are needed.

A particular problem with most types of gas sensors is that they are not completely specific. Thus a sensor designed for one particular gas is also likely to respond to some other gases to varying degrees. Clearly this can lead to problems such as false alarms or ambiguous information.

A further problem that can occur with sensors, which depend in one way or another on adsorption and/or catalysed reactions, is the poisoning of the active surface or catalyst in the sensing element, leading to loss of sensitivity. Lead and silicon compounds and, in some cases, gases such as hydrogen sulphide are well known examples of such poisons.

In order to overcome or alleviate these problems it is common practice to filter the gas before it reaches the sensor. The filter material is chosen to remove the catalyst poison or the interfering gas or gases, while still allowing the gas of interest to pass through. Thus, for example, active carbon can be used to remove lead compounds while still letting gases like methane through; a chemical adsorbent such as soda lime can be used to remove acid gases such as sulphur dioxide and hydrogen sulphide while still letting gases like carbon monoxide through. In a few cases it may be possible to use a catalyst as the filter material with, for example, the gas to be filtered from air oxidising preferentially on the chosen catalyst. In most cases the filtering will depend on physical adsorption or chemical reaction. In all cases and particularly with physical adsorption or chemical reaction it will readily be seen that the filter will have a limited capacity. The capacity will depend on the intrinsic capacity and amount of the filter material, which it is always desirable to keep as low as possible in the interests of compactness and factors such as response time, on the throughput of gas and on the concentration of the species to be removed. In gas sampling systems the flow rate is usually in the range from about 500 mls per minute up to a few liters per minute. In a diffusion operating system the free convection of gas is usually considered to be equivalent to a flow rate of about 500 mls per minute, or larger in draughty conditions.

In practice frequent filter changes are liable to be necessary to ensure integrity of operation and unambiguous results.

It is an objective of this invention to provide a compact integrated filter-sensor system which nevertheless has a long, greatly extended, service life.

According to the present invention a filter is provided between a diffusion barrier and the sensing element of the gas sensor. Accordingly, since the gas passing through the filter must first pass through the diffusion barrier, its flux is substantially reduced, and the effective life of the filter is increased correspondingly. This can be utilised either by using the same amount of filter material as previously and changing it far less frequently or by using a much reduced quantity of filter material, so taking up the benefit in the form of size reduction, or by a combination of the two.

If the life of the filter is as long as that of the sensor, the filter can be made an integral part of the sensor construction. However, it is preferred to arrange for the filter to be readily de-mountable from the sensor assembly so that it can be changed if necessary. For this purpose the diffusion barrier component will also need to be de-mountable, to give access to the filter.

Examples of gas sensor in accordance with the invention will now be described in more detail with reference to the accompanying drawings, in which.

Figure 1:
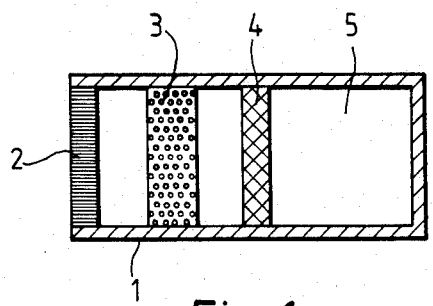
FIG. 1 is a generalised diagrammatic sectional view.

FIG. 1 illustrates the principle involved and shows a housing 1 which carries a diffusion barrier 2, a filter 3 and a gas sensing element 4. Space 5 to the right of the sensing element 4 is for other sensor components of the particular gas sensor being used. As can be seen, gas reaching the filter 3 has first to pass through the diffusion barrier 2 so that its flux is substantially reduced, thus leading to the benefits already described.

Figure 2:
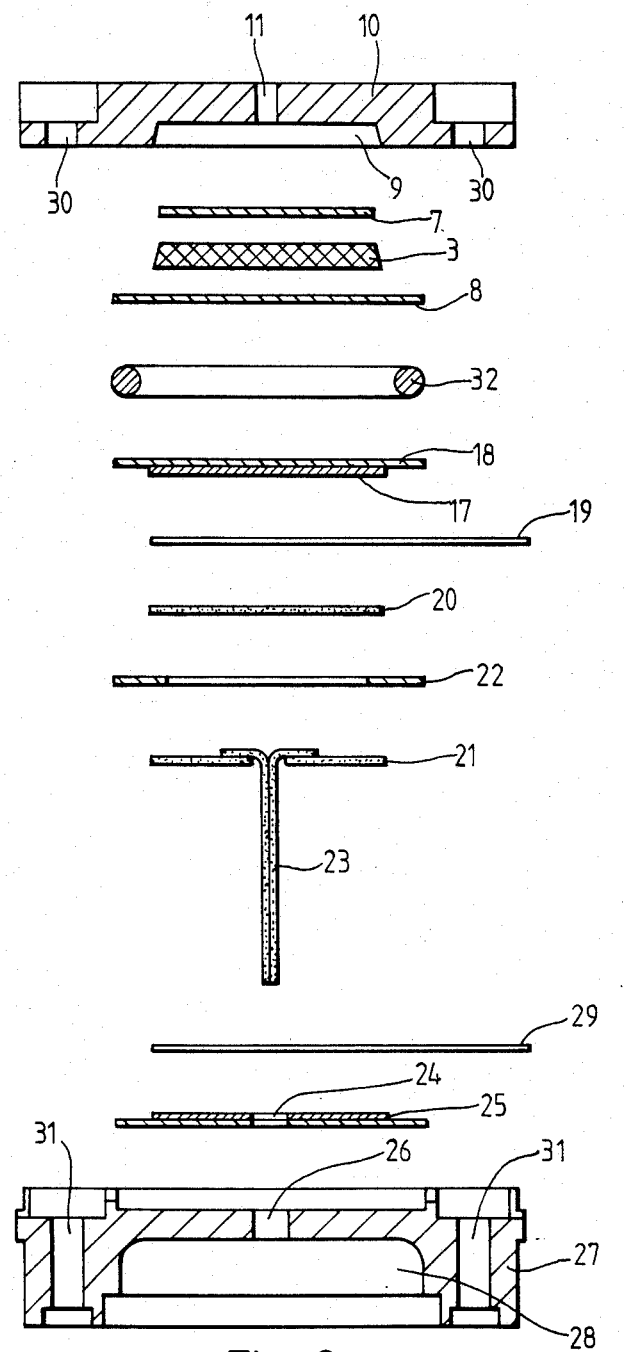
FIG. 2 is an exploded sectional view of a specific construction of sensor.

FIG. 2 shows the general principle of FIG. 1 as applied to an electro-chemical gas sensor of the same basic construction as that described in British specification No. 2,094,005 A. Using the same reference numerals as in FIG. 1 for the main components, the filter 3 is contained between two porous membranes 7 and 8 and fits into a cavity 9 in a top plate 10 which includes a diffusion barrier in the form of a capillary 11. The other components of the sensor are a sensing electrode 17 which is carried on a layer of porous PTFE 18, being provided with a current lead 19. Porous hydrophilic insulating separators 20 and 21 are fitted on either side of a washer 22 and a wick 23 extends through a hole 24 in a counter electrode 25 and through a hole 26 in a base plate 27 into an electrolyte reservoir 28. The counter electrode 25 has a current lead 29 and the complete assembly is held together by bolts passing through holes, two of which are seen at 30 and 31 in the top plate 10 and the base plate 27 respectively, a compressive edge seal being provided by a resilient O-ring 32. After assembly, the reservoir 28 is primed with electrolyte and sealed with a cover plate (not shown). The principle of operation requires no further description since it is identical with that of the sensor described in the earlier specification referred to above.

After assembly the filter 3 forms an integral part of the construction of the sensor as a whole in that it canot be removed without dismantling the complete sensor. The construction illustrated in FIG. 2 is therefore useful when the life of the filter, which is increased to a major extent by virtue of the construction in accordance with the invention, is comparable with that of the sensor as a whole so that the filter does not need to be changed during the whole life of the sensor.

Figure 3:
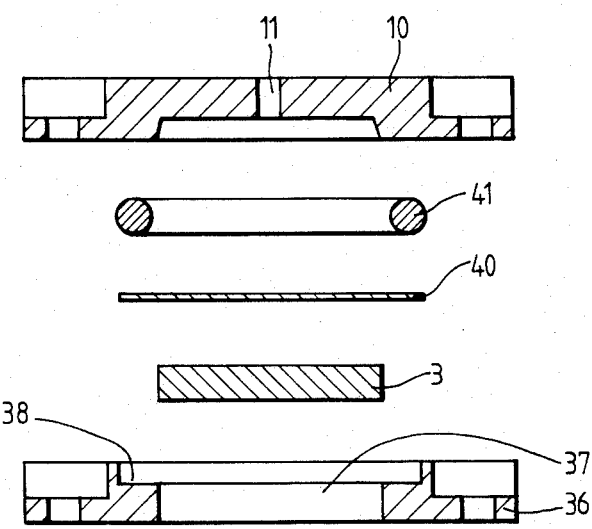
FIG. 3 is a view similar to FIG. 2 of a modified construction of sensor.

If, as is sometimes the case, the filter needs to be changed at least once during the life of the sensor, the modified construction of FIG. 3 is preferably adopted. In this Figure, the components which correspond to those of FIG. 2 are indicated by the same reference numerals and the top plate 10 which includes the diffusion barrier 11 is readily de-mountable so as to allow the filter 3 to be changed without difficulty. The components including and below the O-ring 32 are identical with those of FIG. 2 and are therefore not illustrated. During assembly an additional plate 36 is bolted in position on top of the components just mentioned in place of the top plate 10. This plate 36 is formed with a large central hole 37 for the reception of the filter 3 and a recess 38 to accept a porous membrane 40 and an O-ring 41, these components being held in position by fitting of the top plate 10, which can be held in position by extended portions of the same bolts as used for holding the plate 36. It will thus be understood that the top plate 10 together with the components 40 and 41 can be removed to change the filter 3 without disturbing the remainder of the assembly in any way.

Using the sensor shown in FIGS. 2 and 3 as an example, the order of magnitude of the benefit given by the present invention can be illustrated. Thus for such a sensor, whose sensitivity to carbon monoxide is limited by the diffusion barrier 11 to 0.1 $\mu$A per ppm, it can be calculated from first principles—since 1 gram mole of carbon monoxide will generate 2 Faradays or 1.93 $10^5$ coulombs—that the diffusion flux of carbon monoxide will be 3.11 $10^{-11}$ gm. mols per minute per ppm or at 20° C., 7.47 $10^{-7}$ mls per minute per ppm. To a first approximation the diffusion rates of gases are inversely proportional to the square roots of their molecular weights. If the filter 3 was fitted for the purpose of removing an interfering gas y of molecular weight M, the flux of y to the filter would be $$7.47 \cdot 10^{-7} (28/M)^{\frac{1}{2}}$$

mls per minute per ppm.

This flux can be compared with that applying to a conventional filter placed outside the sensor where, as was seen earlier, the filter has to cope with flow rates of the order of 500 mls per minute of total gas and perhaps more. The flux of the interfering gas y to the filter would therefore be of the order of $500 \times 10^{-6}$ or $5 \times 10^{-4}$ mls per minute per ppm or perhaps more. Depending slightly on the value of M it can be seen from this example that, in round terms, the filter used according to this present invention would receive the interfering gas at only about (1/700)th of the rate of the conventional filter.

The same filter used in arrangements according to the present invention could therefore be expected to last about seven hundred times as long, e.g. a life of one week would become a life of approaching ten years, a month about thirty eight years, and so on. This well illustrates the dramatic improvement made possible by the present invention.

The following are examples of the use of a sensor as illustrated in FIGS. 2 and 3 for specific purposes.

EXAMPLE 1

A sensor as illustrated in FIG. 3 was designed for the measurement of carbon monoxide in flue gas and the filter 3 was designed to remove sulphur dioxide which is an interfering constituent in flue gas. The filter material was 0.7 g. of manganese dioxide in a layer 3 mm thick and 18 mm diameter. The assembly was tested with gas containing 500 ppm sulphur dioxide and the resulting interference was less than 1 ppm carbon monoxide equivalent and remained below this level in a test of continuous exposure lasting forty two days, i.e., 21,000 $SO_2$ ppm days. In the absence of the filter, the interference would have been 350 ppm carbon monoxide equivalent.

EXAMPLE 2

A sensor similar to that described in Example 1 but constructed in accordance with FIG. 2 included a filter 3 composed of 0.4 g manganese dioxide in a bed 2 mm thick and 18 mm diameter. In a continuous exposure at 500 ppm of sulphur dioxide for twenty days, followed by 1000 ppm for thirty one days so far, the interference remained below 1.5 ppm carbon monoxide equivalent.

EXAMPLE 3

A sensor constructed in accordance with FIG. 2, which normally had an equal response to carbon monoxide and hydrogen was converted to a sensor capable of measuring hydrogen with negligible carbon monoxide interference with the use of a filter 3 composed of 0.6 g of a silver oxide—manganese dioxide catalyst in a bed 2.5 mm thick and 18 mm diameter. When tested with 227 ppm carbon monoxide the interference was 1.3 ppm hydrogen equivalent.

Although in the examples illustrated the diffusion barrier is in the form of a capillary, any type of barrier may be used that suitably restricts the difffusion flux. Examples are non-porous plastic membranes, porous bodies or sinters or a diffusion barrier operating on the principle of Knudsen diffusion as described in British specification No. 2,049,952.

Although the illustrated examples include electrochemical gas sensing elements, any type of sensing element can be used to generate a suitable signal from the active gas diffusing to it. Other examples are catalytic gas detection elements and semi-conductor gas detecting elements.

The choice of filter material will obviously depend on the nature of the interfering gas or gases that need removing. The filter may take the form of a prefabricated filter element or may simply be in the form of powder or granules packed in a cavity between the diffusion barrier and the sensing element.

We claim:

1. An electrochemical gas sensor for the continuous measurement of a gas comprising housing means, sensing means within said housing means including electrolytic means for generating output current, diffusion barrier means for severely restricting the flux of gas into said housing means to an extent sufficient to insure the output current of the sensor is controlled by the diffusion flux of gas through said diffusion barrier means so that the output current is a direct function of the concentration of gas being sensed and separate filter means of particulate material mounted between said diffusion barrier and said sensing means, said filter means being subjected to a substantially reduced flux of gas since said diffusion barrier means provides diffusion control to such a degree that the life of said filter means is substantially extended and said filter means being substantially inert to the gas being sensed but capable of removing at least one interfering gas from said gas being sensed wherein the degree of flux restriction by said diffusion barrier in relation to the amount of filter material is such that the sensor is capable of exposure to the interfering gas, without significant interference to the signal of the sensor for the gas being sensed, in an amount on an equivalency basis of at least 21,000 $SO_2$ ppm days when SO$_2$ is the interfering gas and CO is the gas to be sensed.

2. An electrochemical gas sensor according to claim 1 further comprising securing means fixedly securing together said housing means, said sensing means, said diffusion barrier means and said filter means whereby said filter means forms an integral part of said diffusion barrier means and said sensing means.

3. An electrochemical gas sensor according to claim 1 further comprising first securing means fixedly securing together said housing means and said sensing means and second securing means removably securing said filter means and said diffusion means to said housing means whereby said filter means is demountable so as to permit ready replacement.

* * * * *